United States Patent [19]

Jaeger et al.

[11] 4,058,534
[45] Nov. 15, 1977

[54] THERAPEUTICALLY EFFECTIVE NICOTINATES AND N-OXIDE NICOTINATES OF ALIPHATIC AMINES

[75] Inventors: Karl-Heinz Jaeger, Oberggenen, Germany; Willy Herbrand, deceased, late of Gengenbach, Germany, by Elisabeth Herbrand nee Lauterbach, heiress

[73] Assignee: Solco Basel AG, Birsfelden, Switzerland

[21] Appl. No.: 687,765

[22] Filed: May 19, 1976

Related U.S. Application Data

[63] Continuation of Ser. No. 558,325, March 14, 1975, abandoned, which is a continuation of Ser. No. 359,363, May 11, 1973, abandoned, which is a continuation of Ser. No. 109,980, Jan. 26, 1971, abandoned.

[51] Int. Cl.$^2$ .......................................... C07D 213/54
[52] U.S. Cl. ...................... 260/295.5 S; 260/294.8 G; 260/295.5 R; 424/266
[58] Field of Search ................... 260/295.5 R, 295.5 S, 260/294.8 G

[56] References Cited

U.S. PATENT DOCUMENTS 3,622,587  11/1971  Carlson et al. ................ 260/295.5 R

OTHER PUBLICATIONS

Delalande, Chem. Abstracts, vol. 68, (26) Item No. 117,139x, June 24, 1968.
Burger, Medicinal Chemistry, Third Edition, Part Two, Wiley-Interscience, pp. 1158-1159, RS 403 B8 c.2 (1970).

*Primary Examiner*—Alan L. Rotman
*Attorney, Agent, or Firm*—Flynn & Frishauf

[57] ABSTRACT

Aliphatic amine nicotinates (I) and N-oxide nicotinates (II) of the formulae

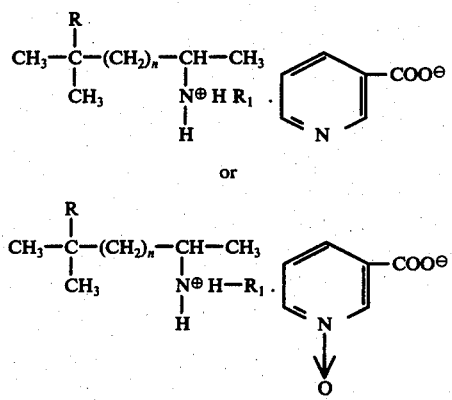

have advantageous therapeutic properties, particularly for dilating blood vessels.

3 Claims, No Drawings

THERAPEUTICALLY EFFECTIVE NICOTINATES AND N-OXIDE NICOTINATES OF ALIPHATIC AMINES

RELATED APPLICATIONS

This application is a continuation of application Ser. No. 558,325, filed Mar. 14, 1975 which, in turn, is a continuation of application Ser. No. 359,363, filed May 11, 1973. The last-mentioned application is a continuation of application Ser. No. 109,980, filed Jan. 26, 1971. Said applications Ser. Nos. 109,980, 359,363 and 558,325 have been abandoned.

The present invention relates to novel therapeutically effective nicotinates and N-oxide nicotinates of aliphatic amines.

The therapeutically active compounds are represented by the general formulae

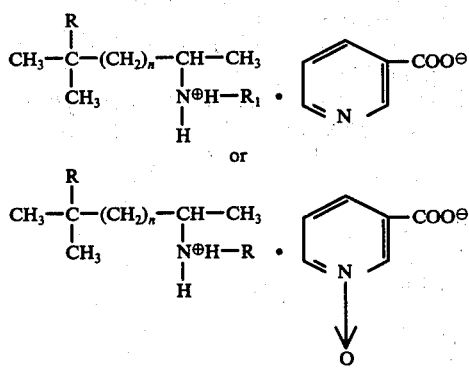

wherein R is hydrogen or a hydroxyl or a thiol group; $R_1$ is hydrogen or a lower alkyl group ($C_{1-2}$) and n is a whole number between 1 and 4.

It is known that lower aliphatic amines and aminoalcohols have sympathikomimetic properties and influence the blood pressure in various ways depending on the constitution of the patient to which they are administered. In particular aminoalcohols, for example, 6-methyl-6-hydroxyl-2-amino-heptane, have effects on the heart similar to strophanthin. The blood pressure is influenced partly by a constriction of the blood vessels and partly by the heart enhancing (cardiotonic) effect of the aminoalcohol.

Nicotinic acid, particularly in the upper half of the body, causes dilation of vessels with simultaneous improvement of blood circulation. Blood pressure has a tendency to drop.

It has been found, surprisingly, that the new therapeutic agents are easily water soluble and thus suitable for parenteral application, and not only for local or peroral application.

The therapeutically active agents which are also locally very well tolerated, are particularly characterized by special pharmacological properties: by increasing, for a short time, the volume of the heart and simultaneous, reasonable dilation of (blood) vessels, and a substantial increase in blood circulation, particularly with small vessels of the brain. The average blood pressure, in general, remains practically unchanged. Similarly, the heart beat frequency (pulse rate) is not increased. The energy consumption of the heart is decreased in comparison with the work being done, so that economy of heart action results.

Particularly the N-oxide nicotinates, with their semipolar oxygen linkage, are excellent in their effectiveness for relatively long time periods.

Preparation of the new compounds is obtained by reaction of free bases with nicotinic acid or a nicotinic acid oxide, in a suitable solvent such as methyl or ethyl alcohol to form salt-like compounds as indicated by the following reaction formulae:

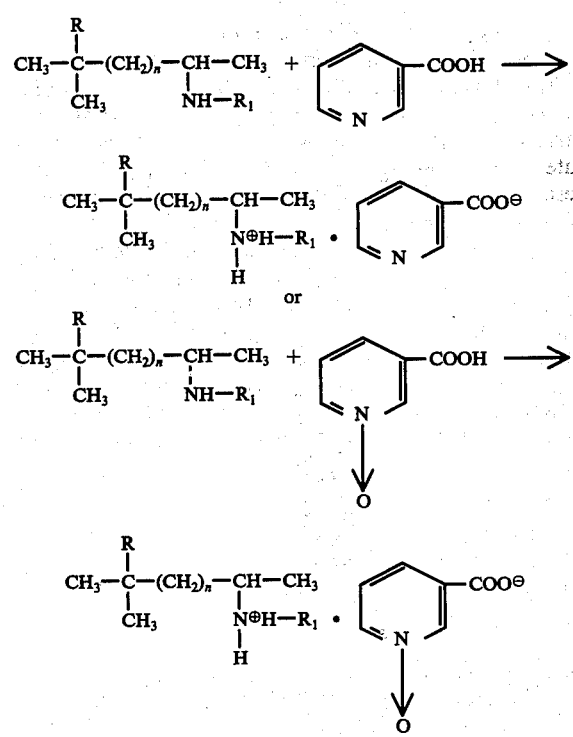

Amine hydrochlorides can be reacted with aqueous solutions of alkali metal salts, particularly with sodium salts of the acids. After removal of water, the new compounds are separated from the alkali metal chlorides by solvents and purified in conventional manner.

EXAMPLE

Preparation of 6-methyl-6-hydroxy-2-amino-heptane-nicotinate

In a 500 ml beaker 29 grams(0.2 mole) of 6-methyl-6-hydroxy-2-amino heptane are dissolved in 150 ml of methyl alcohol. In the above general formula, R is OH, $R_1$ is hydrogen and n is 3. A suspension of 24.6 g (0.2M) of nicotinic acid in 150 ml of methanol is added, to the beaker while stirring the contents thereof. After a short period, a clear solution is formed. This is placed in a 500 ml round-bottom flask and is heated for 1 hour to boiling, with reflux. Thereafter, the solvent is distilled off and remaining traces are removed in a water jet vacuum. The remaining syrup, yellow in color, is stirred with petroleum ether. Crystallization occurs slowly. Small colorless crystals which are formed, are recrystallized from a mixture of isopropyl alcohol and acetone.

The yield of desired product is 48 grams (90% of theoretical). The melting point is 90°-92° C.

Similarly, the methyl substituted 6-methyl-2-amino-heptane-nicotinic acid (with R = H) is formed from equimolar amounts of the reactants, which also have equally desirable pharmacological properties of the character mentioned above.

If, instead of nicotinic acid as a reactant, a N-oxide nicotinic acid is used, then a corresponding N-oxide compound is formed, as indicated above. The N-oxide compounds which are formed are characterized by a particular long activity in a host.

Thus, other typical compounds include:
6-methyl-6-hydroxy-2-amino-heptane-N-oxide nicotinate
6-methyl-2-amino-heptane-nicotinate
6-methyl-2-amino-heptane-N-oxide nicotinate.

The above described examples illustrate heptyl compounds, that is, compounds in which $n$ is 3. Compounds formed from amines in which $n$ is 1, 2 or 4 and substituted urea homologs, in accordance with present test results, also have such advantageous and novel pharmacological properties.

The advantage of the heptaminol-nicotinate-N-oxide-acid-esters produced according to invention is shown by comparison with the usual heptaminol-hydrochloride in the isolated Guinea-pig vestibule. While the known heptaminol has only a short-lasting positive inotropic effect, an equally effective dose of the new substance shows a permanent effect, lasting for hours, which is justified by the chemical constitution. For clinical purposes nearly the same quantities are required, the subject product exerting a retarding effect.

The use of the new compounds is justified by their stronger, quicker and longer-lasting effect on heart, circulation and respiration, with substantially the same dosage as previously known penetration stimulators.

We claim:
1. A nicotinate N-oxide salt having the following structure

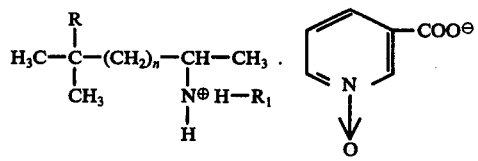

wherein R is hydrogen, or a hydroxyl or thiol group, $R_1$ is hydrogen or a $C_1$ or $C_2$ alkyl group, and $n$ is a whole number from 1 to 4.

2. A compound of claim 1, 6-methyl-6-hydroxy-2-amino-heptane-N-oxide nicotinate.

3. A compound of claim 1, 6-methyl-2-amino-heptane-N-oxide nicotinate.

* * * * *